United States Patent [19]

Terashima et al.

[11] Patent Number: 5,348,889

[45] Date of Patent: Sep. 20, 1994

[54] METHOD FOR CORRECTING A CALIBRATION CURVE

[75] Inventors: Masaaki Terashima; Hajime Makiuchi, both of Saitama, Japan

[73] Assignee: Fuji Photo Film Co., Ltd., Kanagawa, Japan

[21] Appl. No.: 940,770

[22] Filed: Sep. 4, 1992

Related U.S. Application Data

[63] Continuation of Ser. No. 598,903, Oct. 11, 1990, abandoned.

[30] Foreign Application Priority Data

Oct. 13, 1989 [JP] Japan .................. 1-265281

[51] Int. Cl.$^5$ .................. G01N 31/00; G01N 25/00
[52] U.S. Cl. .................. 436/8; 364/571.01; 364/571.02
[58] Field of Search .................. 210/416.1; 364/571.01, 364/571.02, 571.05, 573, 497-500; 436/8

[56] References Cited

U.S. PATENT DOCUMENTS

| | | | |
|---|---|---|---|
| 3,992,158 | 11/1976 | Przybylowicz et al. | 435/14 |
| 4,959,796 | 9/1990 | Hidaka et al. | 364/497 |
| 5,083,283 | 1/1992 | Imai et al. | 364/497 |
| 5,126,952 | 6/1992 | Kildal-Brandt et al. | 364/571.02 |

FOREIGN PATENT DOCUMENTS 0272407 6/1988 European Pat. Off. .

OTHER PUBLICATIONS

Patent Abstracts of Japan, vol. 012390, Gr. P772, Oct. 18, 1988; & JP 63-132,166 An-88-19433, Derwent Publications Ltd., London.
Patent Abstracts of Japan, vol. 012278, GR P738, Aug. 1, 1988; JP A-63-058,164 An-88-109031, Derwent Publications Ltd., London.
Patent Abstracts of Japan, vol. 012441, Gr P789, Nov. 21, 1988; JP A-63-169,539 (Hitachi Ltd.).
D. L. Massart et al "Chemometrics: a textbook", 1988, pp. 75-92, Elsevier Amsterdam, Chapter 5, Calibration Paragraph 7, paragraphs 3-5.

Primary Examiner—James C. Housel
Assistant Examiner—Milton I. Cano
Attorney, Agent, or Firm—McAulay Fisher Nissen Goldberg & Kiel

[57] ABSTRACT

An improved calibration method for calibrating the measured value of an analyte in a liquid sample by referring to a calibration curve drawn by plotting the interrelation between the calibration values of n (n is an integer of not less than 2) calibrators containing different contents of the analyte and the measured values of the analyte contained in respective calibrators. In the improved method provided by the invention, the function of the calibration curve is determined by a first step of estimating an imaginal point, the imaginal point either corresponding to a calibration value larger than the uppermost value of the n calibrators and vicinal to the upper limit of the determination range of the analyte or corresponding to a calibration value smaller than the lowermost value of the n calibrators and vicinal to the lower limit of the determination range of the analyte or a calibration value vicinal to the zero value, and a second step of determining the function of the calibration curve by plotting the imaginal point with two to n measured values.

26 Claims, 2 Drawing Sheets

METHOD FOR CORRECTING A CALIBRATION CURVE

This is a continuation of application Ser. No. 07/598,903, filed Oct. 11, 1990, now abandoned.

BACKGROUND OF THE INVENTION

1. Field of the Invention

The present invention relates to an improvement in calibration of measured values obtained by analyzing liquid samples. More particularly, it provides a calibration method wherein the measured values distributed in a wide range can be calibrated or corrected even when standard samples or calibrators containing an analyte in the concentration of limited range can be prepared.

2. Description of the Related Art

In the conventional quantitative analysis of an analyte contained in a liquid sample, the content of analyte in a test sample is determined by measuring an optical density (absorbancy or optical density of the transmitting or reflected light) of the liquid sample after it is subjected to a proper chemical or enzymatic reaction. In such a method, it is a common practice to determine the content of analyte by using a standard curve (commonly referred to as "calibration curve") which has been preliminarily drawn by plotting the interrelation between the known contents of analyte in the standard samples and the optical densities of the standard samples.

However, a number of standard samples must be prepared and examined to draw a standard curve, and thus cumbersome and time-consuming operations are needed therefor. Particularly when a liquid sample obtained from a living body, such as whole blood, plasma or serum, is used as in the case of a clinical assay, it is difficult to prepare always many standard samples (body fluids) each containing a known content of an analyte. To obviate such a difficulty, it has been proposed and practised to prepare a tentative standard curve which is corrected or calibrated by finding the difference or error from the standard curve. In detail, only a few standard samples or calibrators are examined to find measured values which are used to correct the standard curve to prepare a calibration curve which is used for the determination of real measured values of respective samples.

For example, calibrators containing standard values (calibration values; The term "calibration value" used throughout the specification means the given value for which calibration is to De made, and may be referred to as "real value" or "correct value") of H, M and L are subjected to the same assaying procedure to find optical densities or other proper parameters from which real measured values h, m and l are found by referring to the standard curve. The interrelation between the standard values H, M and L and the real measured values h, m and l are plotted to draw a calibration curve as shown in FIG. 2, and the measured value of each examined sample is corrected by using the thus drawn calibration curve. In an automated analyzer, the function of the calibration curve (generally in the form of a quadratic equation) is determined from the data (l, L), (m, M) and (h, H) by the least squares method to obtain the following correction equation of:

$$Y = \alpha + \beta X + \gamma X^2$$

Then, the measured value is corrected by using the thus obtained correction equation. When the differences in content between the standard values (calibration values) L, M and H are sufficiently large as is the case illustrated in FIG. 2, the effect of curvature of the calibration curve (i.e. the contribution of the term of second order) is small even if the measured values l, m and h are varied independently, so that the measured values distributed in a wide range can be appropriately corrected by the use of the calibration curve.

However, if the differences in content of the standard correct values L, M and H are not large enough, the correct value above the uppermost standard value H and the correct value below the lowermost standard value L tend to contain large errors. Particularly when the measured values l, m and h are varied in the manner as shown in FIG. 3, the calibration curve has an extreme value within the determination range to make it impossible to correct the measured values.

Such a problem arises, for example, in a dry analysis method wherein a dry analysis element is used to analyze an analyte in a liquid sample taken from a living body fluid, such as whole blood, plasma or serum.

The dry analysis element is generally composed of plural layers including, for example, a reagent layer, a porous spreading layer, etc., laminated sequentially on a transparent support. An aqueous liquid sample is spotted on the spreading layer to migrate into the reagent layer which is colored by the action of the analyte contained in the sample. The density of the colored reagent layer is determined by measuring the optical density of the reflected light, and the quantity or content of the analyte contained in the sample is determined by means of colorimetric method. Specific examples of dry analysis element are disclosed in U.S. Pat. Nos. 2,846,808, 3,036,893, 3,368,872 and 3,992,928, Unexamined Japanese Patent Publication Nos. 53888/1974 (corresponding to U.S. Pat. No. 3,992,158), 164356/1980 (corresponding to U.S. Pat. No. 4,292,272), 222769/1985 (corresponding to EP 0 162 302A), 4959/1986 (corresponding to EP 0 166 365A) and 90859/1980 (corresponding to U.S. Pat. No. 4,258,001), Clinical chemistry, 24, 1335–1350, (1978), Analytical Chemistry, 55 (4), 498–514, (1983) and Clinical Chemistry, 27, 1287–1290, (1981).

The liquid sample spotted on the spreading layer spreads on the spreading layer to cover a generally circular zone having an area substantially in proportion to the volume of the spotted sample, and then liquid ingredients migrate into the reagent layer while the solid ingredients are filtered off. As a result, a substantially constant volume of aqueous liquid sample is fed to each unit area of the reagent layer. This function is known as a spreading function or metering function. However, the spreading function is significantly affected by the properties viscosity, specific gravity, pH, etc.) of the spotted aqueous liquid sample. Accordingly, when an analyte contained in a body fluid, such as whole blood, plasma, serum or urine, is to be analyzed, it is preferable to use a calibrator which has properties resembling the body fluid taken from a living body. For example, when albumin or a total protein in blood is quantitatively analyzed, used calibrators are prepared by dissolving lyophilized human blood serum to have proper standard contents. However, the properties of the calibrators are significantly differentiated from those of the body fluids of natural origin as the content of albumin or total protein is varied in a wide range. For this reason, the difference between the lowermost content of analyte and the uppermost content of analyte in the calibrators cannot be set large enough to cover a wide determination range. As a result, when a calibration curve is drawn by using the least squares method, adequate calibration cannot be made within a wide range since an extreme value is found in the thus drawn calibration curve at the worst case.

OBJECTS AND SUMMARY OF THE INVENTION

Accordingly, an object of this invention is to provide an improved method for calibrating a measured value of an analyte contained in a liquid sample accurately within a wide range.

A more specific object of this invention is to provide an improved method for calibrating a measured value of an analyte contained in a liquid sample by using a calibration curve which is drawn by plotting the interrelation between the calibration values of a few calibrators containing different contents of the analyte and the measured values of the analyte contained in respective calibrators, the calibration curve being modified by extrapolating an imaginal point.

The aforementioned object of this invention is achieved by the provision of an improved method in the calibration method for calibrating the measured value of an analyte in a liquid sample by referring to a calibration curve drawn by plotting the interrelation between the calibration values of n (n is an integer of not less than 2) calibrators containing different contents of said analyte and the measured values of said analyte contained in respective calibrators, the improved method wherein the function of said calibration curve is determined by a first step of estimating an imaginal point, said imaginal point either corresponding to a calibration value larger than the uppermost value of said n calibrators and vicinal to the upper limit of the determination range of said analyte or corresponding to a calibration value smaller than the lowermost value of said n calibrators and vicinal to the lower limit of the determination range of said analyte or a calibration value vicinal to the zero value, and a second step of determining the function of said calibration curve by plotting said imaginal point with two to n measured values.

In a preferred embodiment, said calibration value of said imaginal point is the upper limit of the determination range. In another preferred embodiment, said calibration value of said imaginal point is zero value.

BRIEF DESCRIPTION OF THE DRAWINGS

The principle and a presently preferred embodiment of this invention will be described with reference to appended drawings in which.

DETAILED DESCRIPTION OF THE INVENTION

The principle of this invention will be initially described with reference to FIG. 1 for better understanding of the invention.

Figure 1:
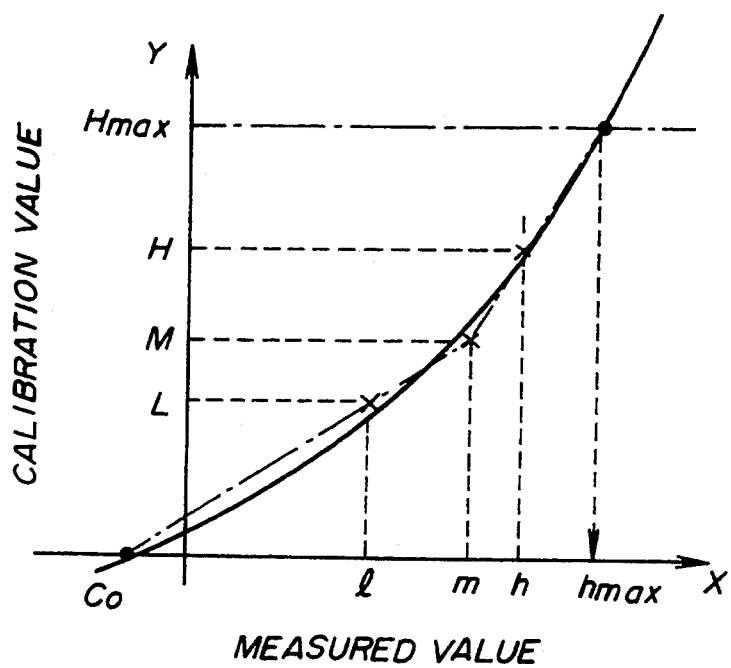
FIG. 1 is a graph illustrating the principle of this invention.

Three calibrators containing known standard calibration values H, M and L of an analyte are assayed in the same process for the quantitative analysis of the analyte to find the measured values l, m and h, and the co-ordinates (H, h), (M, m) and (L, l) are plotted as shown in FIG. 1.

The co-ordinates (imaginal calibration value, imaginal measured value) of an imaginal point is then taken. When it is desired to take an imaginal point above the uppermost point of the calibrators, the imaginal calibration value of the imaginal point is preferably close to the upper limit of the determination range, and more particularly it is preferred that the imaginal calibration value of the imaginal point is the upper limit of the determination range. When it is desired to take an imaginal point below the lowermost point of the calibrators, it is preferable that the imaginal calibration value of the imaginal point is close to zero value of the content of analyte or close to the lower limit of the determination range. In general, it is particularly preferred that the calibration value of the imaginal point is zero value when the subsequent mathematical processing is taken into account. The imaginal measured value corresponding to the imaginal calibration value will be referred to as "estimated measured value" which will be estimated by the method described hereinafter.

The imaginal measured value corresponding to the calibration value $H_{max}$ close to the upper limit of the determination range will be represented by $h_{max}$, and the imaginal measured value at the zero value (correct value=0) will be represented by $C_0$. The upper limit of the determination range means the upper limit value of the analyte within the determination range, and the zero value means that the content of analyte is zero. The imaginal measured values $h_{max}$ and $C_0$ are measured.

When the calibration curve to be drawn is represented by a function of m order, (m+1) values including (l,L), - - - , (m,M), - - - , (h,H), are measured (or plural measured values may be obtained by repeating the analyzing operations for plural times for the three points (l,L), (m,M) and (h,H) depending on the order of the calibration function, values $h_{max}$ and $C_0$ are found. In a preferred curve) to determine the function of a curve of (m−1) order by the least squares method. From the thus determined function, values $h_{max}$ and $C_0$ are found. In a preferred embodiment of this invention, the calibration curve is represented by a function of second order. Generally in case where the calibration curve is represented by a function of second order, an equation of the first order, i.e. a function representing a linear line, is determined from three points (l,L), (m,M) and (h,H), and then the co-ordinates of the point ($h_{max}$, $H_{max}$) may be fixed by finding the point at which the linear line intersects with the line represented by Y=$H_{max}$ and the co-ordinates of the point ($C_0$, 0) may be fixed by the point at which the linear line intersects with the X axis.

Alternatively, the point ($C_0$, 0) is fixed by extending the line connecting the two points (l,L) and (m,M) and then finding the point at which the extension intersects with the X axis; and the point ($h_{max}$, $H_{max}$) is fixed by extending the line connecting the two points (m,M) and (h,H) and then finding the point at which the extension intersects with the line represented by $Y = H_{max}$.

By connecting the five points $(C_0, 0)$, $(l,L)$, $(m,M)$, $(h,H)$ and $(h_{max}, H_{max})$, a calibration curve (shown by the real line in FIG. 1) may be drawn. Measured values lying out of the range of from l to h can be corrected by using the thus drawn calibration curve.

Two alternative methods for taking an imaginal point have been described. However, it has been found that the calibration values of the points beyond the lowermost and uppermost values of the calibrators are deviated to have errors when all of the n calibration values of the calibrators are used to draw the calibration curve due to the influence of the lowermost and uppermost calibration values of the calibrators. In order to eliminate such an error, when an imaginal point is taken in a range above the uppermost point of the calibrators, it is recommended to exclude the lowermost pair of the calibration value and measured value; and similarly the uppermost pair of the calibration value and measured value should be excluded when an imaginal point is taken in a range below the lowermost point of the calibrators. In other words, when n calibrators are used, the measured value of an imaginal point taken in a range above the uppermost measured value of the used n calibrators should be estimated by drawing a calibration curve by using 2 to $(n-1)$ pairs of the calibration and measured values of the calibrators excluding the lowermost pair of the measured and calibration values; whereas the measured value of an imaginal point taken in a range below the lowermost value of the used n calibrators should be estimated by drawing a calibration curve using 2 to $(n-1)$ pairs of the calibration and measured values of the calibrators excluding the uppermost pair of the measured and calibration values.

When the imaginal measured value is estimated only by using the higher two points of the n calibrators, the imaginal measured value $X_{max}$ at the upper limit of the determination range may be calculated from the following equation of:

$$X_{max} = \frac{(Y_{max} - Y_{n-1})(X_n - X_{n-1})}{Y_n - Y_{n-1}} + X_{n-1}$$

wherein $X_{max}$ is the imaginal measured value at the upper limit of the determination range, $Y_{max}$ is the upper limit of the determination range, $Y_n$ is the calibration value of the calibrator containing maximum content of said analyte, $Y_{n-1}$ is the correct value of the calibrator containing next to the maximum content of said analyte, $X_n$ is the measured value of the calibrator containing maximum content of said analyte, and $X_{n-1}$ is the measured value of the calibrator containing next to the maximum content of said analyte.

The measured value $X_0$ of the imaginal point having a calibration value of zero may be estimated by the following equation of:

$$X_0 = \frac{Y_1 \cdot X_2 - Y_2 \cdot X_1}{Y_1 - Y_2}$$

wherein $X_0$ is the imaginal measured value corresponding to the zero value of the calibration value, $Y_1$ is the calibration value of the calibrator containing the minimum content of said analyte, $Y_2$ is the calibration value of the calibrator containing next to the minimum content of said analyte, $X_1$ is the measured value of the calibrator containing the minimum content of said analyte, and $X_2$ is the measured value of the calibrator containing next to the minimum content of said analyte.

EXAMPLES

A multi-layered analysis element for the quantitative analysis of albumin was corrected as follows while using Analyzer FDC 5000 which was an automated analyzer for analyzing ingedients contained in blood and produced and sold by Fuji Photo Film Co., Ltd.

The used munti-layered analysis element was the one which is described in Example 1 of Unexamined Japanese Patent Publication No. 49962/1989 (corresponding to U.S. Ser. No. 07/234,465 and EP 0304052A). The multi-layered analysis element comprises a transparent support layer, a water-absorbing layer laminated on the support layer, and a spreading layer made of a knitted fabric and laminated on the water-absorbing layer, the spreading layer being impregnated with a reagent containing Bromocresol Green as an indicator to develop color by the presence of albumin.

Calibrators used for the calibration were prepared as follows. The level L calibrator (Calibration Value: 2.4 g/dl) was prepared by re-dissolving a lyophilized product which had been produced by adding distilled water to the pooled human serum to prepare a solution having the desired content of albumin followed by lyophilization. The level M calibrator (Calibration Value: 3.4 g/dl) was prepared by re-dissolving a product which had been produced from the pooled human serum without any treatment followed by lyophilization. The level H calibrator (Calibration Value: 4.8 g/dl) was prepared by re-dissolving a product which had been produced by adding an ingredient to be analyzed to the pooled human blood serum followed by lyophilization.

A standard curve drawn by plotting co-ordinates determined by using standard samples having known contents was stored in the Analyzer FDC 5000, and a content of the analyte (i.e. measured value) in the examined sample was determined by measuring the optical density of the reflected light found in the multi-layered analysis element.

Each of the level L, M and H calibrators was spotted on the analysis element and incubated at 37° C. for 6 minutes, and then the optical density of the reflected light showing the color change in the analysis element was measured at a wavelength of 640 nm. The test was repeated for three times for each standard sample to obtain the data set forth below.

|  | Calibration Value | Measured Value | Mean Value |
| --- | --- | --- | --- |
| Level L Calibrator | 2.4 g/dl | 2.3 g/dl<br>2.2 g/dl<br>2.1 g/dl | 2.20 g/dl |
| Level M Calibrator | 3.4 g/dl | 3.6 g/dl<br>3.8 g/dl<br>3.8 g/dl | 3.73 g/dl |
| Level H Calibrator | 4.8 g/dl | 4.6 g/dl<br>4.8 g/dl<br>4.5 g/dl | 4.63 g/dl |

Then, the values $C_0$ and $h_{max}$ were calculated by using the following equation. Meantime, the upper limit $H_{max}$ of the analysis element was 6.0 g/dl.

Imaginal Measured Value ($C_0$) at the zero point:

$$C_0 = \frac{Y_L \cdot X_m - Y_M \cdot X_l}{Y_L - Y_M}$$

wherein $Y_L$ is the calibration value of the level L calibrator; $Y_M$ is the calibration value of the level M calibrator; $X_l$ is the measured value of the level L calibrator; and $X_m$ is the measured value of the level M calibrator.

Imaginal Measured Value ($h_{max}$) at the upper limit of the determination range:

$$h_{max} = \frac{(H_{max} - Y_M)(X_h - X_m)}{Y_H - Y_M} + X_m$$

wherein $H_{max}$ is the upper limit of the determination range; $Y_H$ is the calibration value of the level H calibrator; $Y_M$ is the calibration value of the level M calibrator; $X_h$ is the measured value of the level H calibrator; and $X_m$ is the measured value of the level M calibrator. The results of caluculation are as follows:

$C_0 = -1.48$ g/dl $h_{max} = 5.40$ g/dl

Figure 4:
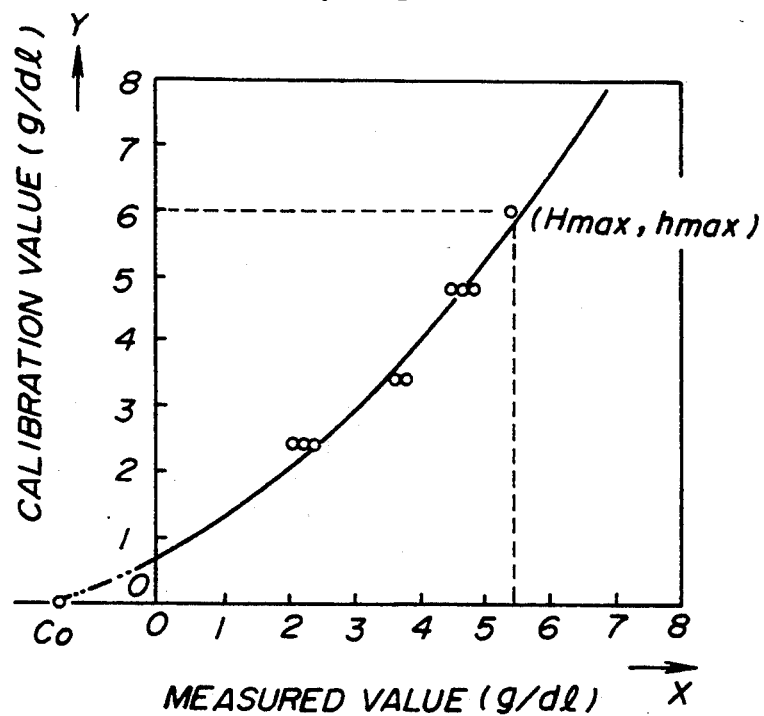
FIG. 4 is a graph showing a calibration curve drawn by the method of this invention.

The function of the calibration curve was computed while using the thus calculated data to draw a calibration curve shown in FIG. 4. By plotting the measured values along the abscissa (X axis) and plotting the calibration values along the ordinate (Y axis), the function of the calibration curve was represented by the following equation.

$Y = 0.07608X^2 + 0.52366X + 0.68746$

Correlation Coefficient $\gamma = 0.98917$

Deviation $S_{yx} = 0.25505$

For the comparison purpose, the function of the calibration curve was computed while using only three points indicating the levels L, M and H to find that the function of the calibration curve was represented by the following equation.

$Y = 0.31172X^2 - 1.16337X + 3.4459$

Correlation Coefficient $\gamma = 0.98897$

Deviation $S_{yx} = 0.16536$

Figure 5:
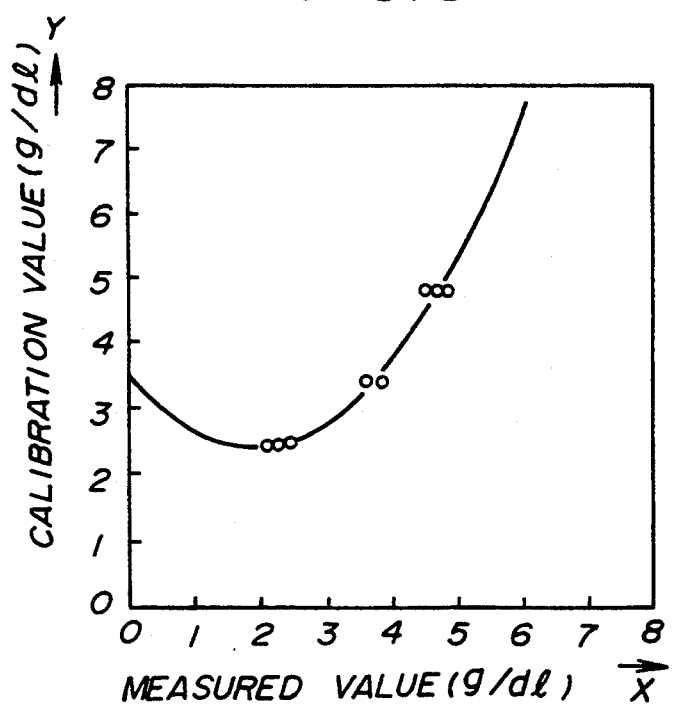
FIG. 5 is a graph showing a calibration curve drawn by a Comparative Example according to the conventional technology.
Figure 1:
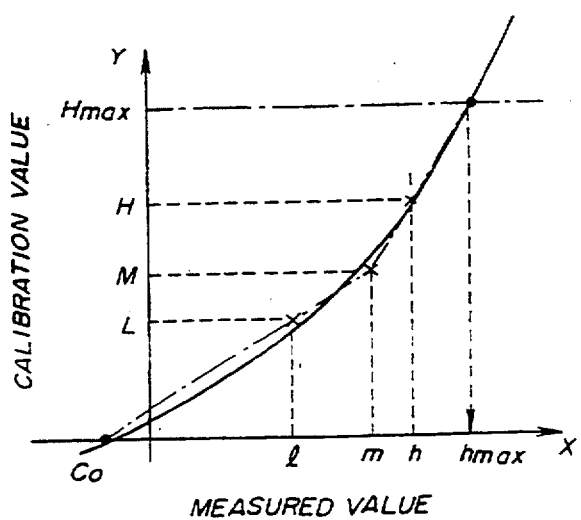
Figure 2:
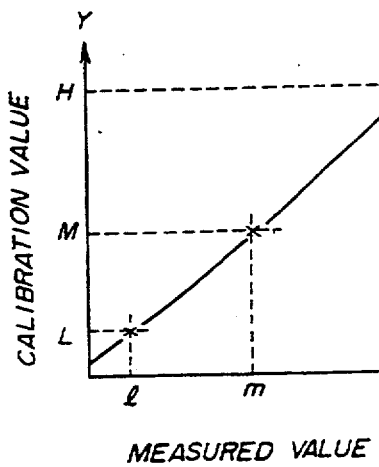
Figure 3:
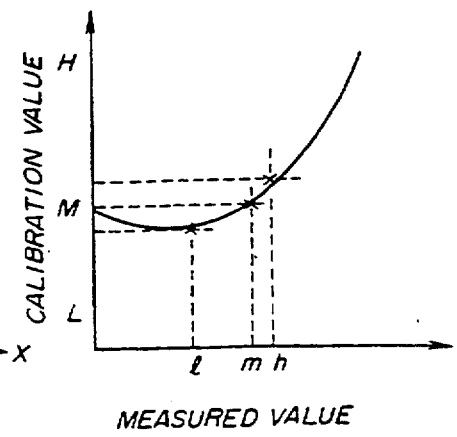

The calibration curve drawn only by using the three points indicating the level L, M and H has an extreme value as shown in FIG. 5.

The meaured values of various samples having different contents of the analyte were corrected by using the thus computed functions.

The Bromocresol Green colorimetric method was used as the standard method for the determination of content of albumin.

TABLE

| Content of albumin Measured by Standard Measuring Method (g/dl) | Measured Content of Albumin Measured by Using Analyzer FDC 5000 (g/dl) | | | | |
|---|---|---|---|---|---|
| | Uncorrected Value | Corrected Value | | Error from the Value Measured by Standard Measuring Method | |
| | | Comparative Example | Example of the invention | Comparative Example | Example of the invention |
| 1.0 | 0.8 | 2.7 | 1.2 | +1.7 | +0.2 |
| 1.3 | 1.1 | 2.5 | 1.4 | +1.2 | +0.1 |
| 2.4 | 2.2 | 2.4 | 2.2 | 0.0 | −0.2 |
| 3.0 | 3.0 | 2.8 | 2.9 | −0.2 | −0.1 |
| 3.4 | 3.7 | 3.4 | 3.7 | 0.0 | +0.3 |
| 4.1 | 4.2 | 4.1 | 4.2 | 0.0 | +0.1 |
| 4.8 | 4.6 | 4.7 | 4.7 | −0.1 | −0.1 |
| 5.3 | 5.0 | 5.2 | 5.2 | +0.1 | −0.1 |
| 5.8 | 5.4 | 5.7 | 5.7 | +0.5 | −0.1 |
| 6.6 | 6.2 | 6.7 | 6.7 | +1.6 | +0.1 |
| 7.8 | 7.3 | 8.6 | 8.6 | +3.8 | +0.8 |

As will be seen from the table set forth above, according to the comparative example, although effective correction can be made within the medium content range, errors induced by correction are too large within the low and high content ranges to indicate that pertinent correction cannot be made within a wide range. On the contrary, according to the example of this invention, effective correction can be made within a wide range covering the range lower than the lowermost standard sample and higher than the uppermost standard sample.

As will be appreciated from the foregoing, measured values distributed in a range out of the content range, within which standard calibrators can be prepared, can be accurately corrected according to this invention.

Although the present invention has been described by referring to an embodiment in which a multi-layered analysis element is used, the invention is not limited thereto but may be applied for correcting the measured values within a wide range over which calibrators cannot be prepared due to problems caused by properties of the sample liquids. Accordingly, it is intended to include all such applications within the scope of the invention.

A calibration curve is drawn, according to the present invention, by plotting points including an imaginal point defined by an imaginal calibration value and an estimated measured value corresponding to the imaginal calibration value, the imaginal calibration value being larger than the uppermost calibration value of the used calibrators or smaller than the lowermost calibration value of the used calibrators. The measured values can be calibrated accurately even if the calibration values corresponding to them are out of the range covered by the calibration values of the used calibrators.

What is claimed is:

1. A method for determining a corrected measured value of an analyte in a liquid sample utilizing a calibration curve comprising the steps of:
   providing a liquid sample of an analyte;
   analyzing the sample to determine a measured value of the analyte;
   preparing a corrected calibration curve by:
   a) subjecting n calibrators, n is an integer and is greater than 2, containing varying known amounts of the analyte to assay in the same process for the quantitative analysis of the analyte so as to obtain the measured values of said n calibrators, said varying known amounts of analyte being referred as the calibration values of said calibrator;
   b) determining a linear function of an uncorrected calibration curve using pairs of coordinates of the calibration values and the measured values of said n calibrators;
   c) estimating a point having a coordinate of a calibration value and a measured value, wherein the calibration value is selected to be;
      i) greater than the uppermost value of said calibration values of said n calibrators but not above the upper limit of a determination range for said analyte,
      ii) less than the lowermost value of said calibration values of said n calibrators but not below the lower limit of the determination range of said analyte; or
      iii) zero value; and
   d) determining a non-linear function of the corrected calibration curve by plotting said estimated point with the coordinates of said calibrators; comparing the measured value of the analyte to the calibration curve; and,
   obtaining a corrected measured value of the analyte.

2. A method for determining a corrected measured value of an analyte in a liquid sample utilizing a calibration curve comprising the steps of:
   providing a liquid sample of an analyte;
   analyzing the sample to determine a measured value of the analyte;
   preparing a corrected calibration curve by:
   a) subjecting n calibrators, n is an integer and is greater than 2, containing varying known amounts of the analyte to assay in the same process for the quantitative analysis of the analyte so as to obtain the measured values of said n calibrators, said varying known amounts of analyte being referred to as the calibration values of said calibrator;
   b) determining a linear function of an uncorrected calibration curve using pairs of coordinates of the calibration values and the measured values of said n calibrators excluding a pair of coordinates having a minimum of the calibration value and measured value;
   c) estimating a point on said uncorrected calibration curve, said estimated point having a coordinate of a calibration value and a measured value, the calibration value of said estimated point being selected to be larger than the uppermost value of said calibration values of said n calibrators but not above the upper limit of a determination range for said analyte, the measured value corresponding to said calibration value and being determined by referring to said uncorrected calibration curve;
   d) determining a non-linear function of the corrected calibration curve by plotting said estimated point with the coordinates of said n calibrators; comparing the measured value of the analyte to the corrected calibration curve; and,
   obtaining a corrected measured value of the analyte.

3. The method of claim 2, wherein said calibration value of said estimated point is the upper limit correct value within the determination range.

4. The method of claim 3, wherein said uncorrected calibration curve is linear, and wherein said measured value is estimated by the following equation:

$$X_{max} = \frac{(Y_{max} - Y_{n-1})(X_n - X_{n-1})}{Y_n - Y_{n-1}} + X_{n-1}$$

wherein;
$X_{max}$ is the measured value at the upper limit of the determination range;
$Y_{max}$ is the calibration value which is the upper limit of the determination range;
$Y_n$ is the calibration value of the calibrator containing the maximum content of said analyte;
$Y_{n-1}$ is the calibration value of the calibrator containing the next to the maximum content of said analyte;
$X_n$ is measured value of the calibrator containing the maximum content of said analyte; and
$X_{n-1}$ is the measured value of the calibrator containing the next to the maximum content of said analyte.

5. The method of claim 2, wherein said corrected calibration curve is determined through the least squares method.

6. The method of claim 2, wherein said liquid sample is analyzed by a dry analysis process.

7. A method for determining a corrected measured value of an analyte in a liquid sample utilizing a calibration curve comprising the steps of:
   providing a liquid sample of an analyte;
   analyzing the sample to determine a measured value of the analyte;
   preparing a corrected calibration curve by:
   a) subjecting n calibrators, n is an integer and is greater 2, containing varying known amounts of the analyte to assay in the same process for the quantitative analysis of the analyte so as to obtain the measured values of said n calibrators, said varying known amounts of analyte being referred to as the calibration values of said calibrator;
   b) determining a linear function of an uncorrected calibration curve using pairs of coordinates of the calibration values and the measured values of said n calibrators excluding a pair of coordinates having the maximum of the calibration value and measured value;
   c) estimating a point on said uncorrected calibration curve, said estimated point having a coordinate of a calibration value and a measured value, the calibration value of said estimated point being selected to be smaller than the lowermost value of said calibration values of said n calibrators but not below the lower limit of the determination range of said analyte, the measured value corresponding to said calibration value and being determined by referring to said uncorrected calibration curve;

d) determining a non-linear function of the corrected calibration curve by plotting said estimated point with the coordinates of said calibrators;

comparing the measured value of the analyte to the corrected calibration curve; and, obtaining a corrected measured value of the analyte.

8. The method of claim 7, wherein said calibration value of said estimated point is the zero value.

9. The method of claim 8, wherein said uncorrected calibration curve is linear, and wherein said measured value is estimated by the following equation:

$$X_0 = \frac{Y_1 X_2 - Y_2 X_1}{Y_1 - Y_2}$$

wherein;

$X_0$ is the measured value corresponding to the zero value of the uncorrected calibration curve;

$X_1$ is the calibration value of the calibrator containing the minimum content of said analyte;

$Y_2$ is the calibration value of the calibrator containing the next to the minimum content of said analyte;

$X_1$ is the measured value of the calibrator containing the minimum content of said analyte; and $X_2$ is the measured value of the calibrator containing the next to the minimum content of said analyte.

10. The method of claim 7, wherein said corrected calibration curve is determined through the least squares method.

11. The method of claim 7, wherein said liquid sample is analyzed by a dry analysis process.

12. A method for determining a corrected measured value of an analyte in a liquid sample utilizing a calibration curve comprising the steps of:

providing a liquid sample of an analyte;

analyzing the sample to determine a measured value of the analyte;

preparing a corrected calibration curve by:

a) subjecting n calibrators, n is an integer and is greater than 2, containing varying known amounts of the analyte to assay in the same process for the quantitative analysis of the analyte so as to obtain the measured values of said n calibrators, said varying known amounts of analyte being referred to as the calibration values of said calibrator;

b) determining a linear function of a first uncorrected calibration curve using pairs of coordinates of the calibration values and the measured values of said n calibrators excluding a pair of coordinates having the minimum of the calibration value and measured value;

c) estimating a first point on said first uncorrected calibration curve, said first point having a coordinate of the first calibration value and first measured value, the first calibration value being selected to be larger than the uppermost value of said calibration values of said n calibrators but not above the upper limit of a determination range for said analyte, the first measured value corresponding to said first calibration value and being determined by referring to said first uncorrected calibration curve;

d) determining the linear function of a second uncorrected calibration curve using pairs of coordinates of the calibration values and the measured values of said n calibrators excluding a pair of coordinates having the maximum of the calibration value and measured value;

e) estimating a second point on said second uncorrected calibration curve, said second point having a coordinate of the second calibration value and second measured value, the second calibration value being selected to be smaller than the lowermost value of said calibration values of said n calibrators but not below the lower limit of the determination range of said analyte, the second measured value corresponding to said second calibration value and being determined by referring to said second uncorrected calibration curve;

f) determining a non-linear function of the corrected calibration curve by plotting said first and second estimated points with the coordinates of said calibrators;

comparing the measured value of the analyte to the corrected calibration curve; and, obtaining a corrected measured value of the analyte.

13. The method of claim 12, wherein said first calibration value is the upper limit value of the determination range.

14. The method of claim 13, wherein said first uncorrected calibration curve is linear, and wherein said first measured value is estimated by the following equation:

$$X_{max} = \frac{(Y_{max} - Y_{n-1})(X_n - X_{n-1})}{Y_n - Y_{n-1}} + X_{n-1}$$

wherein;

$X_{max}$ is the first measured value at the upper limit of the determination range;

$Y_{max}$ is the first calibration value which is the upper limit of the determination range;

$Y_n$ is the calibration value of the calibrator containing the maximum content of said analyte;

$Y_{n-1}$ is the calibration value of the calibrator containing the next to the maximum content of said analyte;

$X_n$ is the measured value of the calibrator containing the maximum content of said analyte; and $X_{n-1}$ is the measured value of the calibrator containing the next to the maximum content of said analyte.

15. The method of claim 12, wherein said second calibration value is the zero value.

16. The method of claim 15, wherein said second uncorrected calibration curve is linear, and wherein said second measured value is estimated by the following equation:

$$X_0 = \frac{Y_1 X_2 - Y_2 X_1}{Y_1 - Y_2}$$

wherein;

$X_0$ is the second measured value corresponding to the zero value of the second uncorrected calibration curve;

$Y_1$ is the calibration value of the calibrator containing the minimum content of said analyte;

$Y_2$ is the calibration value of the calibrator containing the next to the minimum content of said analyte;

$X_1$ is the measured value of the calibrator containing the minimum content of said analyte; and $X_2$ is the measured value of the calibrator containing the next to the minimum content of said analyte.

17. The method of claim 12, wherein said corrected calibration curve is determined through the least squares method.

18. The method of claim 12, wherein said liquid sample is analyzed by a dry analysis process.

19. The method of claim 3, wherein said corrected calibration curve is determined through the least squares method.

20. The method of claim 4, wherein said corrected calibration curve is determined through the least squares method.

21. The method of claim 8, wherein said corrected calibration curve is determined through the least squares method.

22. The method of claim 9, wherein said corrected calibration curve is determined through the least squares method.

23. The method of claim 13, wherein said corrected calibration curve is determined through the least squares method.

24. The method of claim 14, wherein said corrected calibration curve is determined through the least squares method.

25. The method of claim 15, wherein said corrected calibration curve is determined through the least squares method.

26. The method of claim 16, wherein said corrected calibration curve is determined through the least squares method.

* * * * *

UNITED STATES PATENT AND TRADEMARK OFFICE
CERTIFICATE OF CORRECTION

Figure 2:
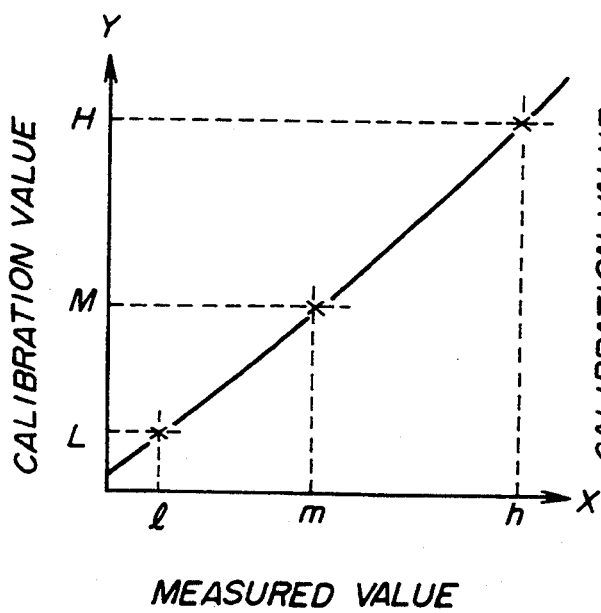
FIG. 2 is a graph showing a calibration curve drawn by the conventional technology when calibrators covering a wide range can be prepared.
Figure 3:
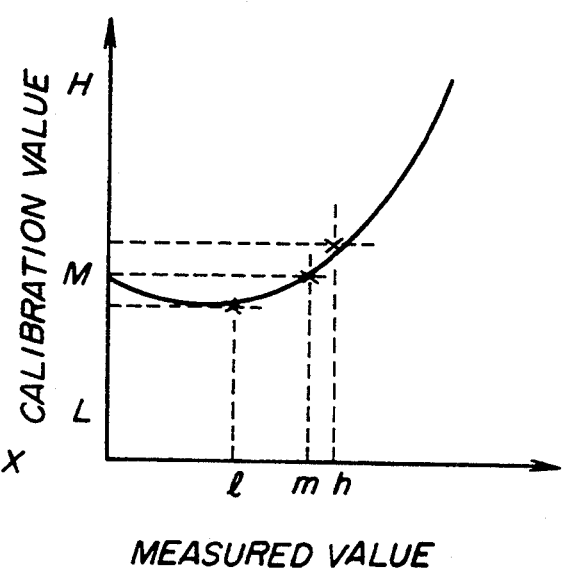
FIG. 3 is a graph showing a calibration curve drawn by the conventional technology when calibrators covering a wide range cannot be prepared.

PATENT NO. : 5,348,889
DATED : September 20, 1994
INVENTOR(S) : Masaaki Terashima, et al It is certified that error appears in the above-indentified patent and that said Letters Patent is hereby corrected as shown below:

IN THE DRAWINGS:

Sheet 1 of 2 should be deleted and substitute therefor attached sheet 1 of 2 (showing Figs. 2 and 3, labeled - Prior Art).

UNITED STATES PATENT AND TRADEMARK OFFICE
CERTIFICATE OF CORRECTION

PATENT NO. : 5,348,889
DATED : September 20, 1994
INVENTOR(S) : Masaaki TERASHIMA, et al It is certified that error appears in the above-indentified patent and that said Letters Patent is hereby corrected as shown below:

Column 1, line 50, change "De" to --be--;

Column 2, line 51, after "properties" insert --(e.g.,--

Column 4, line 14, after "point" change "is" to --are--;
       line 48, after "calibration" delete "function, $h_{max}$ and $C_o$ are found. In a preferred";

Column 6, line 10, after "used" change "munti-layered" to --multi-layered--;

Column 7, line 40, change "caluculation" to --calculation--;

Column 8, line 6, change "meaured" to --measured--.

Signed and Sealed this

Fifteenth Day of August, 1995

Attest:

BRUCE LEHMAN

*Attesting Officer*     *Commissioner of Patents and Trademarks*